US008282645B2

(12) United States Patent
Lawrence et al.

(10) Patent No.: US 8,282,645 B2
(45) Date of Patent: Oct. 9, 2012

(54) METATARSAL BONE IMPLANT CUTTING GUIDE

(75) Inventors: Bruce R. Lawrence, Oceanside, CA (US); Rebecca Hawkins Wahl, Escondido, CA (US)

(73) Assignee: Solana Surgical, LLC, Oceanside, CA (US)

( * ) Notice: Subject to any disclaimer, the term of this patent is extended or adjusted under 35 U.S.C. 154(b) by 321 days.

(21) Appl. No.: 12/689,155

(22) Filed: Jan. 18, 2010

(65) Prior Publication Data

US 2011/0178524 A1     Jul. 21, 2011

(51) Int. Cl.
*A61F 5/00* (2006.01)
*A61F 2/42* (2006.01)

(52) U.S. Cl. ........................... 606/87; 623/21.19

(58) Field of Classification Search .............. 606/79, 606/82, 86 R, 87, 96, 97; 623/21.11, 21.15, 623/21.17, 21.19
See application file for complete search history.

(56) References Cited

U.S. PATENT DOCUMENTS

| 4,627,425 | A | * | 12/1986 | Reese | 606/87 |
| 5,601,565 | A | * | 2/1997 | Huebner | 606/87 |
| 2005/0228389 | A1 | * | 10/2005 | Stiernborg | 606/79 |
| 2007/0265634 | A1 | * | 11/2007 | Weinstein | 606/87 |
| 2008/0195215 | A1 | * | 8/2008 | Morton | 623/18.11 |
| 2008/0269908 | A1 | * | 10/2008 | Warburton | 623/21.15 |
| 2010/0222782 | A1 | * | 9/2010 | Collazo et al. | 606/89 |
| 2010/0256687 | A1 | * | 10/2010 | Neufeld et al. | 606/289 |
| 2010/0324556 | A1 | * | 12/2010 | Tyber et al. | 606/62 |
| 2011/0077656 | A1 | * | 3/2011 | Sand et al. | 606/96 |
| 2011/0093084 | A1 | * | 4/2011 | Morton | 623/21.19 |
| 2011/0288550 | A1 | * | 11/2011 | Orbay et al. | 606/70 |

OTHER PUBLICATIONS

Futura™ Biomedical, The Metal Hemi Toe, brochure, 1998,19-5017 Rev. A, © 1998 Futura Biomedical, San Diego, CA, USA.
Futura™ Biomedical, The Primus Flexible Great Toe Implant, brochure, 1999 ,19-5027 Rev. A, © 1999 Futura Biomedical, San Diego, CA, USA.
Futura™, NEXA, A Tornier Company, Forefoot Implant Arthroplasty Products, brochure, 2004,#19-5058 Rev. C, © 2004-2007 Tornier, Inc., Stafford. TX, USA.
Futura™, Tornier, Forefoot Implant Arthroplasty Products, brochure, 2004,#19-5058 Rev. D, © 2004-2008 Tornier, Inc., Stafford. TX, USA.

* cited by examiner

*Primary Examiner* — Thomas Barrett
*Assistant Examiner* — Matthew Lawson
(74) *Attorney, Agent, or Firm* — Roeder & Broder LLP

(57) ABSTRACT

A method for guiding a saw blade (22) during preparation of a metatarsal (14) of a foot (10) for a procedure, such as to receive a metatarsal bone implant (20), includes positioning a housing (242) substantially adjacent to the metatarsal (14), coupling an aligner (38) to the housing (242), and aligning a saw guide (30) of the housing (242). The housing (242) includes the saw guide (30) for receiving and guiding the saw blade (22). The foot (10) includes one or more additional metatarsals (142), and the aligner (38) is used to align the saw guide (30) relative to the metatarsal (14) by aligning the aligner (38) to be substantially parallel to and positioned over a longitudinal axis (40) of one of the additional metatarsals (142).

18 Claims, 7 Drawing Sheets

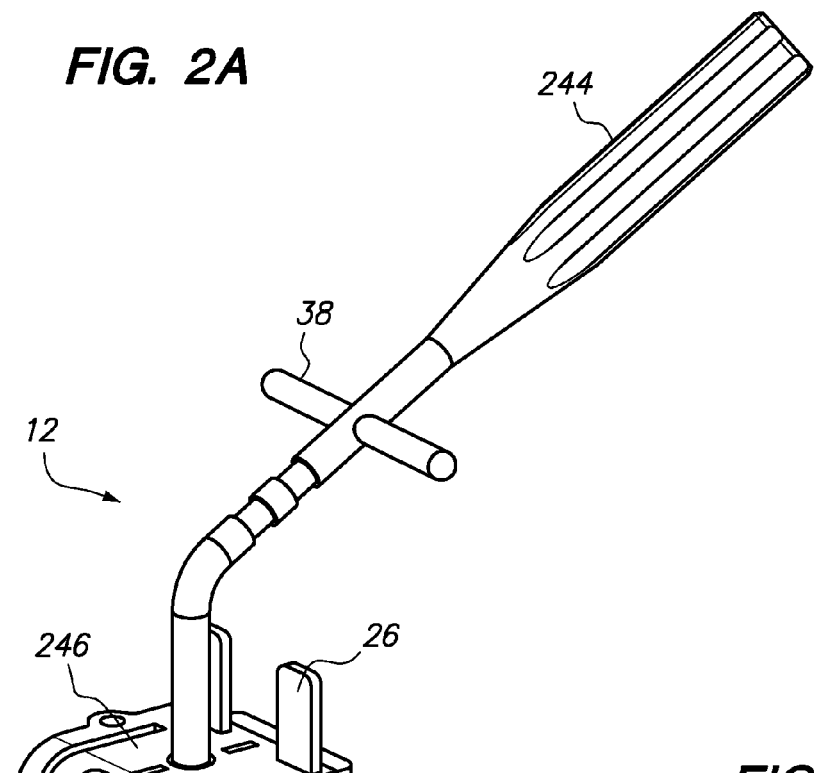
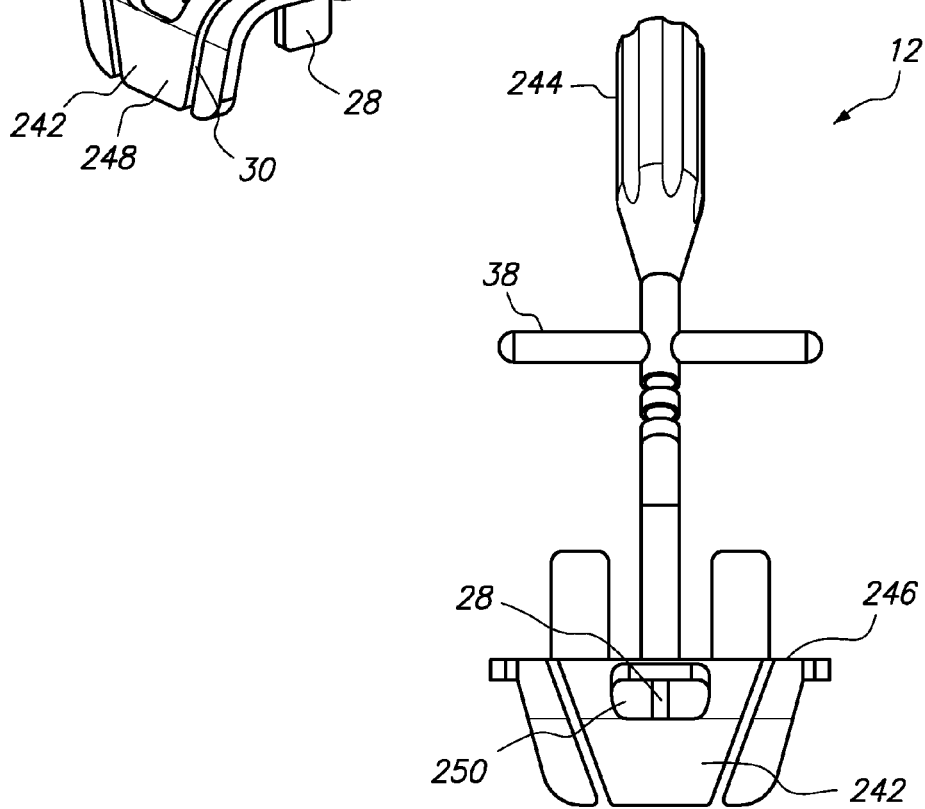

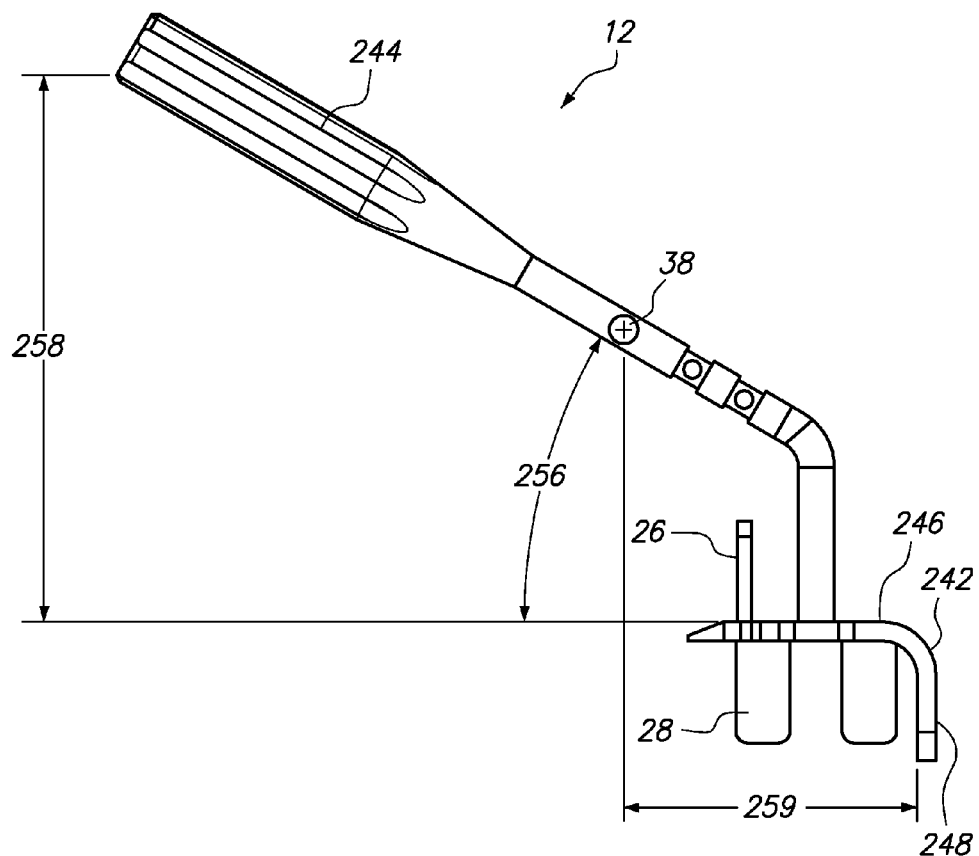
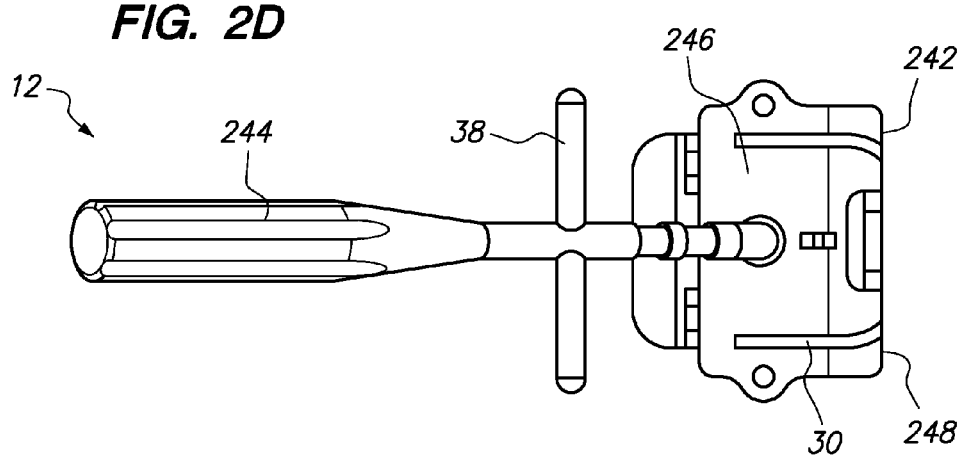

METATARSAL BONE IMPLANT CUTTING GUIDE

BACKGROUND

It is well known that some people have problems with one or more joints in their feet, with particular problems being seen in the forefoot, or the front of the foot. The forefoot includes the metatarsals and the phalanges, with the joint between these bones commonly referred to as the metatarsal phalangeal joint. The majority of disease seen in toe joints affects the head of the first metatarsal, or big toe. Problems with the metatarsal phalangeal joint of a toe, most commonly with the big toe or great toe, include pain and swelling due to rheumatoid arthritis, hallux limitus (where motion is restricted due to abnormal structure or function), hallux rigidus (where motion is severely restricted or absent), pain due to an impacted joint, joint deterioration or deformation often associated with arthritis, and/or unstable or painful joints due to previous surgeries.

Several procedures have been developed to treat these conditions. For example, bone implants are often used to obtain pain relief and improve function of the metatarsal phalangeal joint. However, bone implants can only successfully enable the recipient of the bone implant to obtain pain relief and improve function of the metatarsal phalangeal joint if the bone implant is implanted accurately. In order to be able to implant the bone implant accurately, a portion of the distal end of the metatarsal must be cut and removed to allow the necessary spacing for the bone implant. An implant cutting guide can be used to line up and stabilize the area which is to be cut and removed. Accordingly, there is a need for an implant cutting guide that can accurately and repeatably align the cutting tool, e.g., a bone saw, so as to enable a proper amount of bone to be cut and removed.

SUMMARY

The present invention is directed toward a cutting guide for guiding a saw blade during preparation of a metatarsal of a foot for a procedure, such as to receive a metatarsal implant, the foot including one or more additional metatarsals. In certain embodiments, the cutting guide includes a housing and an aligner. The housing is adapted to be positioned substantially adjacent to the metatarsal. Additionally, the housing includes a saw guide for receiving and guiding the saw blade. The aligner is coupled to the housing. The aligner is used to align the saw guide relative to one of the additional metatarsals.

In some embodiments, the aligner extends substantially perpendicular to the saw guide. Additionally, in certain embodiments, the aligner can be used to be substantially aligned with a longitudinal axis of one of the additional metatarsals.

In certain embodiments, the cutting guide further includes a handle that is secured to the housing. The handle can cantilever in a generally upward direction away from the housing. In one such embodiment, the aligner is a bar that is coupled to the handle and that extends substantially perpendicular to the handle.

In one embodiment, the cutting guide can further include one or more alignment tabs that are secured to and cantilever in a generally downward direction away from the housing. In one such embodiment, the alignment tabs are adapted to be positioned within a joint gap between the metatarsal and a proximal phalanx of the foot.

In certain embodiments, the metatarsal is a first metatarsal. In one such embodiment, the aligner is used to be substantially aligned with a longitudinal axis of a second metatarsal.

In some embodiments, the housing can further include a housing top and a housing side. In such embodiments, the saw guide extends through both the housing top and the housing side. Additionally, the housing can further include a housing axis. In one such embodiment, the saw guide extends through the housing side at a guide angle of between approximately 12 degrees and 25 degrees relative to the housing axis.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 2A is a perspective view of an embodiment of a cutting guide having features of the present invention;

FIG. 2B is a front view of the cutting guide illustrated in FIG. 2A;

FIG. 2C is a side view of the cutting guide illustrated in FIG. 2A;

FIG. 2D is a top view of the cutting guide illustrated in FIG. 2A;

DESCRIPTION

Figure 1A:
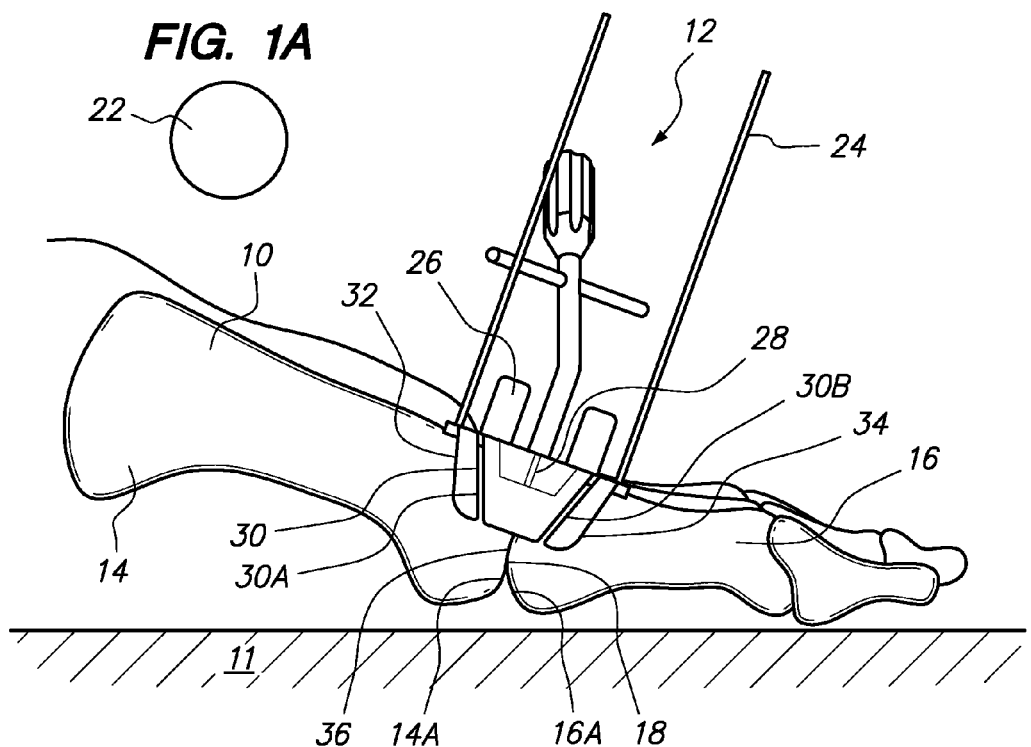
FIG. 1A is a side view of a portion of a foot of a person and an embodiment of a cutting guide having features of the present invention.

FIG. 1A is a side view of a portion of a foot 10, more particularly a left foot, of a person for supporting the person above a surface 11, such as a floor or the ground, and an embodiment of a cutting guide 12 having features of the present invention. The foot 10 includes a metatarsal 14 having a distal end 14A, and a proximal phalanx 16 having a proximal end 16A that is positioned adjacent to the distal end 14A of the metatarsal 14. The distal end 14A of the metatarsal 14 and the proximal end 16A of the proximal phalanx 16 cooperate to form a portion of a metatarsal phalangeal joint 18.

Figure 5:
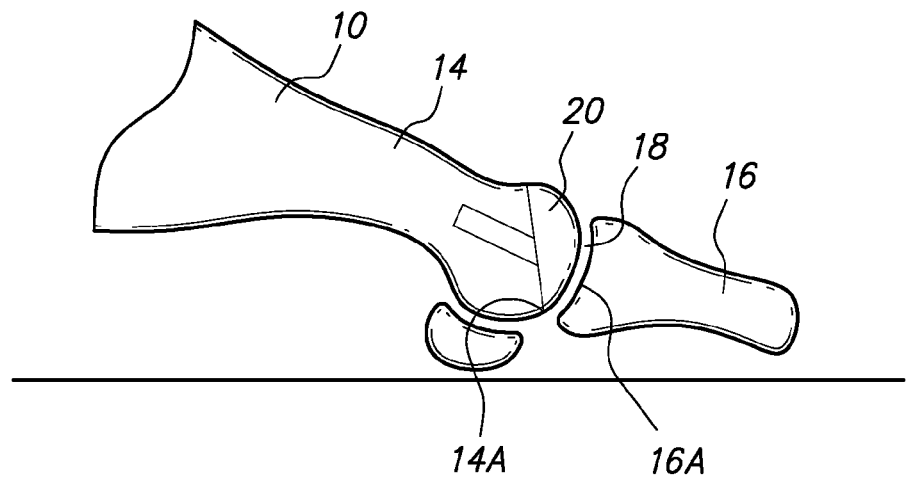
FIG. 5 is a side view of a portion of a foot after a bone implant has been implanted using a cutting guide having features of the present invention.

The cutting guide 12 is designed to be used during the preparation of the metatarsal 14 of the foot 10 to receive a metatarsal bone implant 20 (illustrated in FIG. 5). In particular, the cutting guide 12 is designed for receiving and guiding a saw blade 22 (illustrated as a circle) during the preparation of the metatarsal 14 to receive the metatarsal bone implant 20.

The design of the cutting guide 12 can be varied depending on certain specific criteria, such as the size of the foot 10. In one embodiment, the cutting guide 12 includes a pair of stabilizers 24, one or more retraction tabs 26, one or more alignment tabs 28, and one or more saw guides 30 that receive and guide the saw blade 22 during the cutting of the metatarsal 14. Alternatively, the cutting guide 12 can be designed without one or more of these features. For example, the cutting guide 12 can be designed without the stabilizers 24.

As an overview, the cutting guide 12 of the present invention enables the proper, accurate and repeatable alignment of the saw blade 22 so as to ensure a proper amount of bone can be cut and removed from the metatarsal 14 to create the necessary space for the metatarsal bone implant 20 to be implanted in the metatarsal 14. More specifically, the cutting guide 12 of the present invention is uniquely designed to ensure the proper and accurate alignment of the cutting guide 12 adjacent to the metatarsal 14 and the proximal phalanx 16 to enable the saw blade 22 to be positioned to remove the proper amount and the proper portion of the metatarsal 14 to create the necessary space for the metatarsal bone implant 20.

A suitable metatarsal bone implant 20 that is usable in conjunction with the present invention to ensure the smooth movement of the post-operative metatarsal phalangeal joint 18 without otherwise interfering with the structure, integrity or functioning of the bones of the foot 10 can be found in U.S. patent application Ser. No. 12/421,480 entitled "Metatarsal Bone Implant" as filed by Bruce R. Lawrence and Rebecca Wahl on Apr. 9, 2009. To the extent allowable, the disclosure provided in U.S. patent application Ser. No. 12/421,480 is incorporated herein by reference.

The stabilizers 24 are designed to selectively and fixedly secure the cutting guide 12 to the metatarsal 14 and the proximal phalanx 16 to provide additional stability during use of the cutting guide 12. Stated another way, the stabilizers 24 are designed to inhibit movement of the cutting guide 12 relative to the metatarsal 14 so as to ensure that a proper and accurate cut can be made in the metatarsal 14. As illustrated, the stabilizers 24 can be positioned to extend through a proximal side 32 and a distal side 34 of the cutting guide 12, with one stabilizer 24 selectively and fixedly securing the cutting guide 12 to the metatarsal 14 and the other stabilizer 24 selectively and fixedly securing the cutting guide 12 to the proximal phalanx 16. In certain embodiments, the stabilizers 24 may be K-wires that extend through the cutting guide 12 to selectively and fixedly secure the cutting guide 12 to the foot 10. Alternatively, the stabilizers 24 can be designed to have a different design, shape and/or orientation. Still alternatively, the cutting guide 12 can be designed to include more than two or less than two stabilizers 24.

The one or more retraction tabs 26 are designed to hold the tendons and the skin of the foot 10 out of the way when utilizing the cutting guide 12 to help provide clear and unobstructed access to the metatarsal 14 and the proximal phalanx 16 of the foot 10. In the embodiment illustrated in FIG. 1A, the cutting guide 12 is designed to include two retraction tabs 26. Alternatively, the cutting guide 12 can be designed to have more than two or less than two retraction tabs 26.

The one or more alignment tabs 28 are adapted to be positioned within a joint gap 36 within the metatarsal phalangeal joint 18 between the metatarsal 14 and the proximal phalanx 16 of the foot 10 to assist in properly aligning the cutting guide 12 and, more particularly, the saw guides 30, relative to the metatarsal 14 and the proximal phalanx 16 of the foot 10. Stated another way, the alignment tabs 28 are designed to extend in a generally downward direction away from a majority of the cutting guide 12 and into the metatarsal phalangeal joint 18 to ensure that the saw guides 30 are positioned properly along the length of the foot 10 so as to enable a proper cut in the metatarsal 14. In the embodiment illustrated in FIG. 1A, the cutting guide 12 is designed to include two alignment tabs 28 (only one is visible in FIG. 1A). Alternatively, the cutting guide 12 can be designed to have more than two or less than two alignment tabs 28.

The one or more saw guides 30 are adapted to receive and guide the saw blade 22 during the cutting of the metatarsal 14. In this embodiment, the cutting guide 12 includes a proximal saw guide 30A that is positioned substantially adjacent to a portion of the metatarsal 14 and a distal saw guide 30B that is positioned substantially adjacent to a portion of the proximal phalanx 16. The proximal saw guide 30A is designed to receive and guide the saw blade 22 during the cutting of the metatarsal 14. The cutting guide 12 as provided herein is designed to include both the proximal saw guide 30A and the distal saw guide 30B so that the cutting guide 12 can be effectively used with either a left foot, as illustrated herein in FIG. 1A, or a right foot. It should be noted that when the cutting guide 12 is being utilized with a right foot, the position of the proximal saw guide 30A and the distal saw guide 30B will be reversed. In such a situation, the distal saw guide 30B will function as a proximal saw guide and be positioned adjacent to a portion of the metatarsal 14 and will guide the saw blade 22, and the proximal saw guide 30A will function as a distal saw guide and be positioned adjacent to a portion of the proximal phalanx 16.

Figure 1B:
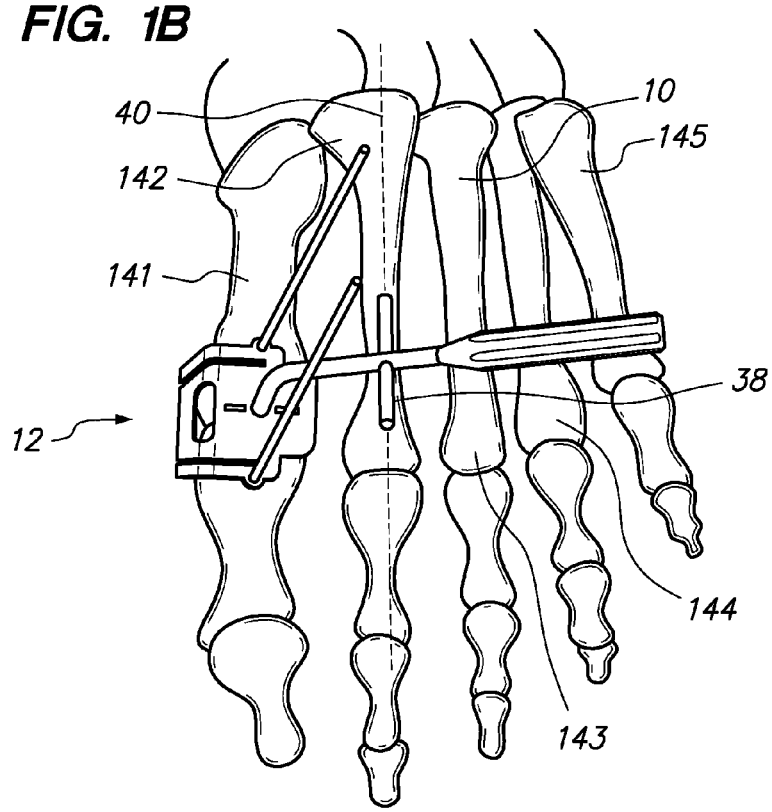
FIG. 1B is a top view of a portion of the foot and the cutting guide illustrated in FIG. 1A.

FIG. 1B is a top view of a portion of the foot 10, more particularly the left foot, and the cutting guide 12 illustrated in FIG. 1A. As illustrated in FIG. 1B, the foot 10 can include a first metatarsal 141, a second metatarsal 142, a third metatarsal 143, a fourth metatarsal 144, and a fifth metatarsal 145, and the cutting guide 12 can be positioned substantially adjacent to the first metatarsal 141. Alternatively, the cutting guide 12 can be positioned substantially adjacent to one of the other metatarsals 142, 143, 144, 145.

As illustrated in FIG. 1B, the cutting guide 12 further includes an aligner 38 that is adapted to be positioned in alignment with and substantially parallel to a longitudinal axis 40 of one of the metatarsals 141, 142, 143, 144, 145. In particular, when the cutting guide 12 is positioned substantially adjacent to the first metatarsal 141, as illustrated in FIG. 1B, the aligner 38 is adapted to be positioned in alignment with and substantially parallel to the longitudinal axis 40 of one of the other metatarsals 142, 143, 144, 145. For example, as shown, the aligner 38 can be positioned in alignment with and substantially parallel to the longitudinal axis 40 of the second metatarsal 142. Alternatively, the aligner 38 can be designed to be positioned in alignment with and substantially parallel to the longitudinal axis 40 of one of the third metatarsal 143, the fourth metatarsal 144, or the fifth metatarsal 145 without altering the teachings as provided herein.

With this design, once the aligner 38 is approximately aligned with the longitudinal axis 40 by the doctor, the saw guide 30 is properly aligned on the first metatarsal 141 so that the first metatarsal 141 can be accurately cut in preparation for the implant 20 (illustrated in FIG. 5).

FIG. 2A is a perspective view of the cutting guide 12 illustrated in FIG. 1A. In this embodiment, the cutting guide 12 includes a housing 242, the one or more retraction tabs 26, the one or more alignment tabs 28, a handle 244, the aligner 38, and the saw guides 30. Alternatively, the cutting guide 12 can be designed without one or more of these components. For example, the cutting guide 12 can be designed without the retraction tabs 26.

The housing 242 is adapted to be positioned adjacent to the metatarsal 14 (illustrated in FIG. 1A) and the proximal phalanx 16 (illustrated in FIG. 1A) of the foot 10 (illustrated in FIG. 1A). In this embodiment, the housing 242 is shaped somewhat similar to a "L" rotated ninety degrees, and includes a housing top 246 that is adapted to be positioned adjacent to an upper surface of the metatarsal 14 and the proximal phalanx 16, and a housing side 248 that is adapted to be positioned adjacent to a side surface of the metatarsal 14 and the proximal phalanx 16. In this embodiment, the housing side 248 is approximately perpendicular to the housing top 246.

As provided above, the retraction tabs 26 are designed to hold the tendons and the skin out of the way when utilizing the cutting guide 12. More particularly, the retraction tabs 26 hold the tendons and the skin out of the way in order to provide clear and unobstructed access to the metatarsal 14 and the proximal phalanx 16 of the foot 10. As illustrated, the retraction tabs 26 are coupled to the housing top 246 of the housing 242 and extend in a generally upward direction substantially perpendicularly away from the housing top 246.

Additionally, as provided above, the alignment tabs 28 are adapted to be positioned within the joint gap 36 (illustrated in FIG. 1A) of the metatarsal phalangeal joint 18 (illustrated in FIG. 1A) between the metatarsal 14 and the proximal phalanx 16 of the foot 10. More particularly, the alignment tabs 28 are adapted to assist in properly aligning the cutting guide 12 and, more particularly, the saw guides 30 relative to the metatarsal 14 and the proximal phalanx 16 of the foot 10. Stated another way, the alignment tabs 28 are designed to extend in a generally downward direction substantially perpendicularly away from the housing top 246 and into the metatarsal phalangeal joint 18 to ensure that the saw guides 30 are positioned properly along the length of the foot 10 so as to enable a proper cut in the metatarsal 14. With this design, the alignment tabs 28 are used to ensure that the appropriate saw guide 30 is positioned properly along the metatarsal 14.

The handle 244 is coupled to the housing top 246 of the housing 242 and cantilevers in a generally upward direction away from the housing top 246. The handle 244 is utilized to assist in positioning of the housing 242 adjacent to the metatarsal 14 and the proximal phalanx 16 of the foot 10.

The aligner 38 is coupled to the housing 242 and is used to align the saw guides 30 relative to one of the metatarsals 141, 142, 143, 144, 145 (illustrated in FIG. 1B). In certain embodiments, the aligner 38 is adapted to be positioned in alignment with and substantially parallel to a longitudinal axis 40 (illustrated in FIG. 1B) of one of the metatarsals 141, 142, 143, 144, 145. In particular, when the housing 242 is positioned adjacent to the first metatarsal 141, the aligner 38 is used to align the saw guides 30 relative to one of the additional metatarsals 142, 143, 144, 145. For example, in one embodiment, when the housing 242 is positioned adjacent to the first metatarsal 141, the aligner 38 is used to align the saw guides 30 relative to the second metatarsal 142. In such embodiment, the aligner 38 can be used to be substantially aligned with and parallel to the longitudinal axis 40 of the second metatarsal 142. Alternatively, the aligner 38 can be used to be substantially aligned with and parallel to the longitudinal axis 40 of the third metatarsal 143, the fourth metatarsal 144 or the fifth metatarsal 145.

FIG. 2B is a front view of the cutting guide 12 illustrated in FIG. 2A. In particular, FIG. 2B illustrates additional features of the housing 242 and the aligner 38 of the cutting guide 12.

As illustrated in FIG. 2B, the housing 242 can include an alignment aperture 250 that enables the user to view the alignment tabs 28 during positioning of the cutting guide 12 relative to the metatarsal 14 (illustrated in FIG. 1A) and the proximal phalanx 16 (illustrated in FIG. 1A). Stated another way, the alignment aperture 250 enables the user to view the alignment tabs 28 to ensure that the alignment tabs 28 are properly positioned within the joint gap 36 (illustrated in FIG. 1A) of the metatarsal phalangeal joint 18 (illustrated in FIG. 1A) between the metatarsal 14 and the proximal phalanx 16.

The design of the aligner 38 can be varied to suit the specific requirements of the cutting guide 12. In the embodiment illustrated in FIG. 2B, the aligner 38 is a cylindrical bar that is coupled to the handle 244 and that extends substantially perpendicular to the handle 244. Moreover, in some embodiments, the aligner 38 extends away from the handle 244 an approximately equal amount on either side of the handle 244. Alternatively, the aligner 38 can have a different design, a different orientation, and/or can be coupled to the housing 242 in a different manner.

Additionally, as illustrated in FIG. 2B, the aligner 38 can be positioned in a substantially parallel relationship with the housing top 246. In some embodiments, the aligner 38 can be designed to be approximately one inch in length. Alternatively, the aligner 38 can be designer to be greater than or less than one inch in length.

FIG. 2C is a side view of the cutting guide 12 illustrated in FIG. 2A. In particular, FIG. 2C illustrates additional features of the retraction tabs 26, the alignment tabs 28 and the handle 244 of the cutting guide 12.

In certain embodiments, the retraction tabs 26 and the alignment tabs 28 can be substantially similar in design. For example, in one embodiment, each of the retraction tabs 26 and each of the alignment tabs 28 can be substantially rectangular in shape and have a width of approximately 0.18 inches, a height of approximately 0.34 inches, and a thickness of approximately 0.04 inches. Additionally, each of the retraction tabs 26 and each of the alignment tabs 28 can further include a tab connector (not illustrated) that is adapted to fit within and be retained within a retraction tab aperture 352 (illustrated in FIG. 3A) or an alignment tab aperture 354 (illustrated in FIG. 3A) included in the housing top 246 of the housing 242. Further, in the embodiment illustrated in FIG. 2C, the retraction tabs 26 are positioned in a substantially parallel relationship relative to the housing side 248, and the alignment tabs 28 are positioned in a substantially perpendicular relationship relative to the housing side 248. Alternatively, the retraction tabs 26 and the alignment tabs 28 can be designed to have a different shape, to have dimensions that are greater than or less than the dimensions provided above, to have a different orientation relative to the housing side 248, and/or to be coupled to the housing 242 in a different manner.

As illustrated in FIG. 2C, the handle 244 is coupled to the housing 242 and initially extends in a generally upward direction substantially perpendicularly away from the housing 242. After the initial perpendicular positioning of the handle 244 relative to the housing 242, another portion of the handle 244 extends at a handle angle 256 relative to the housing 242. In certain embodiments, the handle angle 256 is approximately 30 degrees relative to the housing top 246. Alternatively, the handle angle 256 can be greater than or less than 30 degrees relative to the housing top 246.

Additionally, in certain embodiments, the handle 244 is designed such that when the cutting guide 12 is engaged with the foot 10 (illustrated in FIG. 1A), the end of the handle 244 away from the housing 242 is positioned at a handle height 258 of approximately 1.80 inches relative to the housing top 246. Alternatively, the handle 244 can be designed to have a handle height 258 of greater than or less than 1.80 inches relative to the housing top 246.

Additionally, as illustrated in FIG. 2C, the aligner 38 is spaced apart from the housing side 248 horizontally an alignment distance 259. In one non-exclusive embodiment, the alignment distance 259 is approximately 1.05 inches to 1.12 inches. Alternatively, the alignment distance 259 can be less than approximately 1.05 inches or greater than approximately 1.12 inches.

FIG. 2D is a top view of the cutting guide 12 illustrated in FIG. 2A. In particular, FIG. 2D illustrates additional features of the handle 244 and the aligner 38 of the cutting guide 12.

As illustrated in this embodiment, the handle 244 can be coupled to the housing top 246 of the housing 242 at a point that is substantially centrally located along the housing top 246. Alternatively, the handle 244 can be coupled to the housing 242 at a different point.

Additionally, in this embodiment, the aligner 38 is positioned such that it is substantially parallel to the housing side 248 of the housing 242. Further, the aligner 38 extends substantially perpendicular to the portion of the saw guides 30 that is positioned along the housing top 246 of the housing 242. Alternatively, the cutting guide 12 can be designed so that the aligner 38 has a different orientation relative to the housing side 248 and the saw guides 30.

Figure 2E:
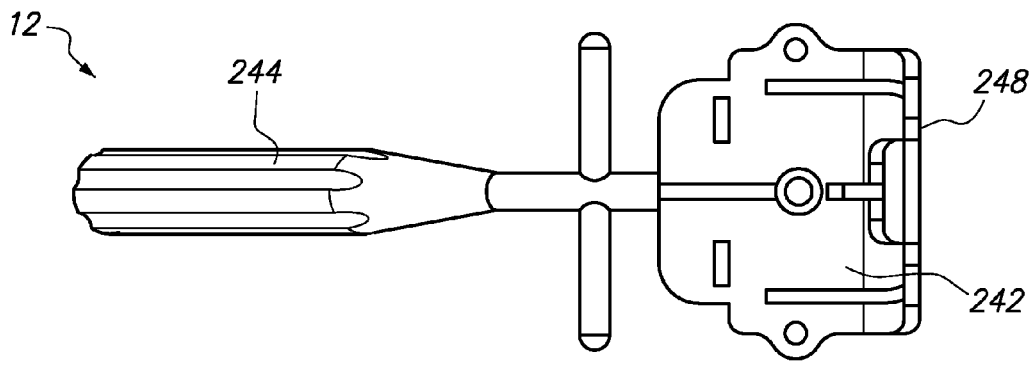
FIG. 2E is a bottom view of the cutting guide illustrated in FIG. 2A.

FIG. 2E is a bottom view of the cutting guide 12 illustrated in FIG. 2A. As illustrated in this embodiment, the handle 244 is substantially perpendicular to the housing side 248 of the housing 242. Alternatively, the cutting guide 12 can be designed so that the handle 244 has a different orientation relative to the housing side 248 of the housing 242.

Figure 3A:
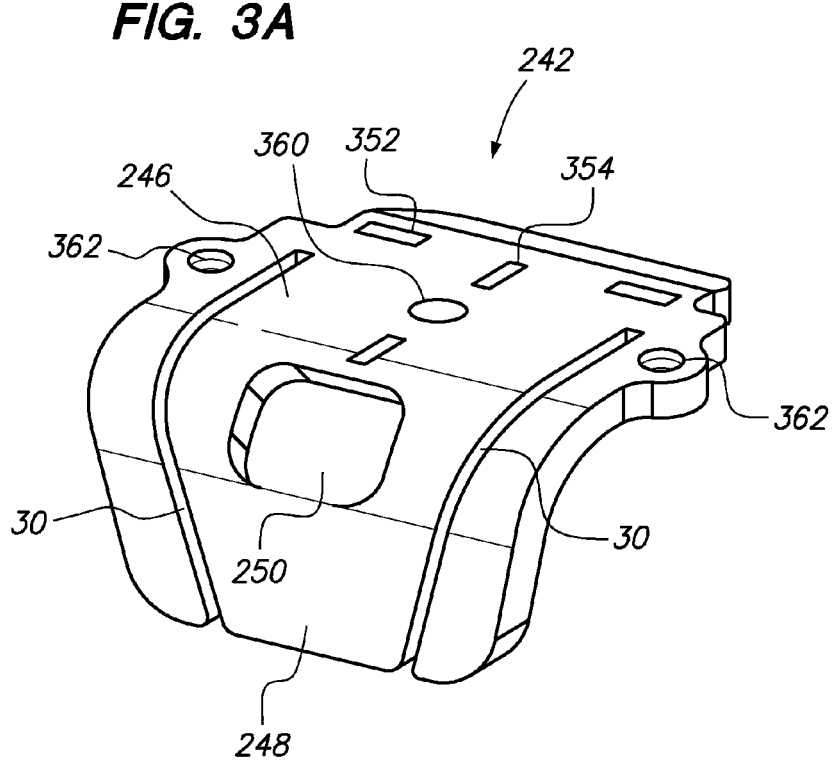
FIG. 3A is a perspective view of an embodiment of a housing usable as part of the present invention.

FIG. 3A is a perspective view of an embodiment of the housing 242 usable as part of the present invention. The design of the housing 242 can be varied depending on the specific requirements of the cutting guide 12 (illustrated in FIG. 2A) and the size of the foot 10 (illustrated in FIG. 1A). In this embodiment, the housing 242 includes the housing top 246, the housing side 248 that cantilevers away from the housing top 246, a handle aperture 360 that is adapted to receive a portion of the handle 244 (illustrated in FIG. 2A), a pair of stabilizer apertures 362 that are adapted to receive the pair of stabilizers 24 (illustrated in FIG. 1A), the alignment aperture 250, one or more retraction tab apertures 352 that are adapted to receive a portion of the one or more retraction tabs 26 (illustrated in FIG. 2A), one or more alignment tab apertures 354 that are adapted to receive a portion of the one or more alignment tabs 28 (illustrated in FIG. 2A), and the pair of saw guides 30.

Figure 3B:
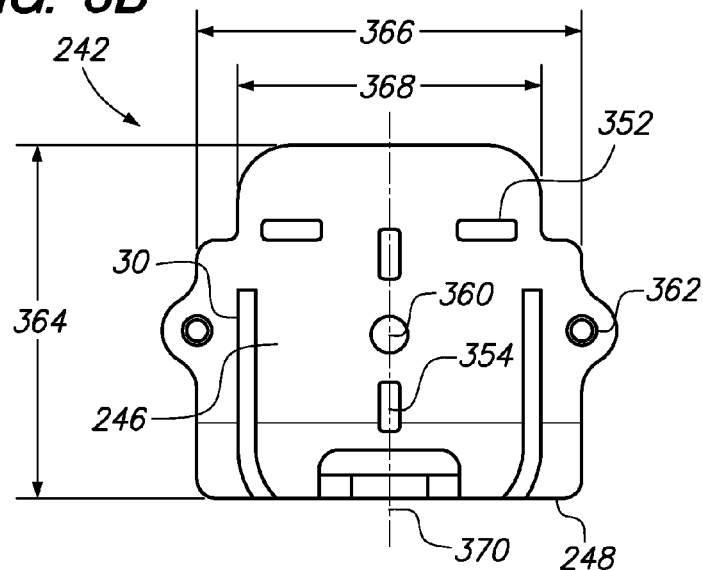
FIG. 3B is a top view of the housing illustrated in FIG. 3A.

FIG. 3B is a top view of the housing 242 illustrated in FIG. 3A. In particular, FIG. 3B illustrates further details of the housing top 246 of the housing 242. As illustrated in FIG. 3B, the housing top 246 of the housing 242 can be somewhat rectangle shaped with a housing length 364 of between approximately 0.84 and 0.91 inches, a greater housing width 366 of between approximately 0.90 and 0.99 inches, and a lesser housing width 368 of approximately 0.70 inches. Alternatively, the housing top 246 can be designed to have a different shape or to have different dimensions. For example, the housing top 246 can be designed to have the housing length 364, the greater housing width 366, and the lesser housing width 368 that are greater than or less than the dimensions mentioned above.

As noted above, the handle aperture 360 is adapted to receive a portion of the handle 244 and to secure the handle 244 (illustrated in FIG. 2A) to the housing top 246 of the housing 242. As illustrated in this embodiment, the handle aperture 360 can be substantially circular in shape and can be centrally located along the housing top 246 of the housing 242. Alternatively, the handle aperture 360 can have a different shape or be positioned at a different location.

Additionally, as noted above, the stabilizer apertures 362 are adapted to receive a portion of the stabilizers 24 (illustrated in FIG. 1A) and to secure the stabilizers 24 to the housing top 246 of the housing 242. As illustrated, the stabilizer apertures 362 can be substantially circular in shape and can be positioned between approximately 0.40 and 0.47 inches from the housing side 248 of the housing 242 and can be evenly spaced on either side of the handle aperture 360. Alternatively, the stabilizer apertures 362 can have a different shape or be positioned at a different location.

Further, as noted above, the alignment tab apertures 354 are adapted to receive a portion of the alignment tabs 28 (illustrated in FIG. 2A) and to secure the alignment tabs 28 to the housing top 246 of the housing 242. As illustrated, the alignment tab apertures 354 can be positioned along a housing axis 370 and can be evenly spaced on either side of the handle aperture 360. Moreover, the alignment tab apertures 354 can be oriented to be substantially perpendicular to the housing side 248 of the housing 242. Alternatively, the alignment tab apertures 354 can have a different shape or be positioned at a different location.

Still further, as noted above, the retraction tab apertures 352 are adapted to receive a portion of the retraction tabs 26 (illustrated in FIG. 2A) and to secure the retraction tabs 26 to the housing top 246 of the housing 242. As illustrated, the retraction tab apertures 352 can be positioned between approximately 0.62 and 0.69 inches from the housing side 248 of the housing 242 and can be evenly spaced on either side of the housing axis 370 and can be oriented to be substantially parallel to the housing side 248 of the housing 242. Alternatively, the retraction tab apertures 352 can have a different shape or be positioned at a different location.

Additionally, the saw guides 30 are positioned substantially evenly spaced on either side of the housing axis 370. In certain embodiments, the saw guides 30 can be positioned between approximately 0.345 inches and 0.415 inches on either side of the housing axis 370. Alternatively, the saw guides 30 can be positioned at a distance of greater than 0.415 inches or less than 0.345 inches away from the housing axis 370. The portion of each of the saw guides 30 that extends through the housing top 246 of the housing 242 is substantially perpendicular to the housing side 248 of the housing 242.

Figure 3C:
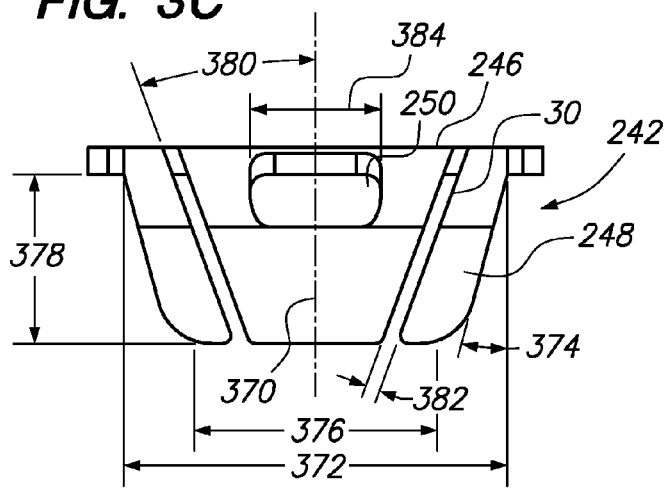
FIG. 3C is a front view of the housing illustrated in FIG. 3A.

FIG. 3C is a front view of the housing 242 illustrated in FIG. 3A. In particular, FIG. 3C illustrates further details of the housing side 248 of the housing 242. As illustrated in this embodiment, the housing side 248 of the housing 242 can be somewhat trapezoid shaped having an outer width 372 of between approximately 0.90 inches and 0.99 inches that tapers down at a taper angle 374 of approximately 15 degrees to an inner width 376 of between approximately 0.68 inches and 0.79 inches, and a housing height 378 of approximately 0.40 inches. Alternatively, the housing side 248 can have a different shape or have different dimensions. For example, the housing side 248 can be designed to have an outer width 372, an inner width 376, a taper angle 374, and a housing height 378 that are greater than or less than the dimensions mentioned above.

As illustrated in FIG. 3C, and as noted above in relation to FIG. 3B, the saw guides 30 are substantially evenly spaced on either side of the housing axis 370. Additionally, in certain embodiments, the saw guides 30 extend through the housing side 248 of the housing 242 at a guide angle 380 relative to the housing axis 370. In certain embodiments, the saw guides 30 can be positioned at a guide angle 380 of between approximately 12 degrees and 25 degrees. For example, as illustrated in FIG. 3C, the saw guides 30 can be positioned at a guide angle 380 of approximately 18 degrees relative to the housing axis 370. Alternatively, the saw guides 30 can be positioned at a guide angle 380 of greater than 18 degrees or less than 18 degrees relative to the housing axis 370. Further, the saw guides 30 can be designed to have a guide width 382 of approximately 0.03 inches. Alternatively, the saw guides 30 can be designed to have a guide width 382 of greater than or less than 0.03 inches.

The alignment aperture 250 enables the user to view the alignment tabs 28 (illustrated in FIG. 2A) as the cutting guide 12 (illustrated in FIG. 1A) is being positioned adjacent to the metatarsal 14 (illustrated in FIG. 1A) and the proximal phalanx (illustrated in FIG. 1A). As shown in FIG. 3C, the alignment aperture 250 can be positioned so that it extends an equal distance on either side of the housing axis 370. Additionally, as illustrated in FIGS. 3B and 3C, the alignment aperture 250 extends along a portion of both the housing top 246 and the housing side 248 of the housing 242. In certain embodiments, the alignment aperture 250 can have an aperture width 384 of approximately 0.31 inches. Alternatively, the alignment aperture 250 can have an aperture width 384 that is greater than or less than 0.31 inches.

Figure 3D:
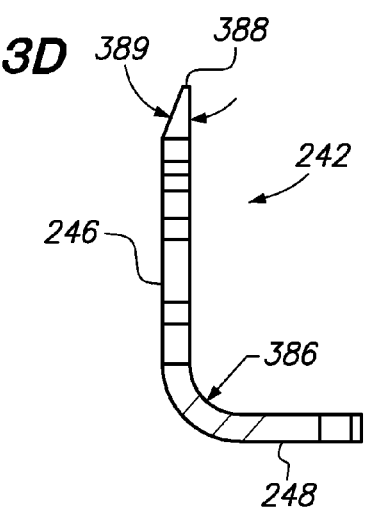
FIG. 3D is a side view of the housing illustrated in FIG. 3A.

FIG. 3D is a side view of the housing 242 illustrated in FIG. 3A. As illustrated, the housing side 248 can be substantially perpendicular to the housing top 246 of the housing 242. Additionally, the housing side 248 and the housing top 246 can be joined by a curved portion 386 that has a radius of approximately 0.125 inches. The curved portion 386 provides the cutting guide 12 (illustrated in FIG. 1A) with a more comfortable fit when the cutting guide 12 is mounted adjacent to the metatarsal 14 (illustrated in FIG. 1A) and the proximal phalanx (illustrated in FIG. 1A). Alternatively, the housing 242 can be designed without the curved portion that joins the housing side 248 and the housing top 246, or the radius of the curved portion 386 can be greater than or less than 0.125 inches.

Further, in certain embodiments, the housing side 248 and the housing top 246 can have a thickness of approximately 0.06 inches, except for an end of the housing top 246 away from the housing side 248, which can have a tapered portion 388 with a minimum thickness of approximately 0.02 inches and a taper angle 389 of approximately 16 degrees. Alternatively, the housing side 248 and the housing top 246 can be designed to have a thickness that is greater than or less than 0.06 inches, and/or the housing top 246 can be designed without the tapered portion 388.

Figure 4A:
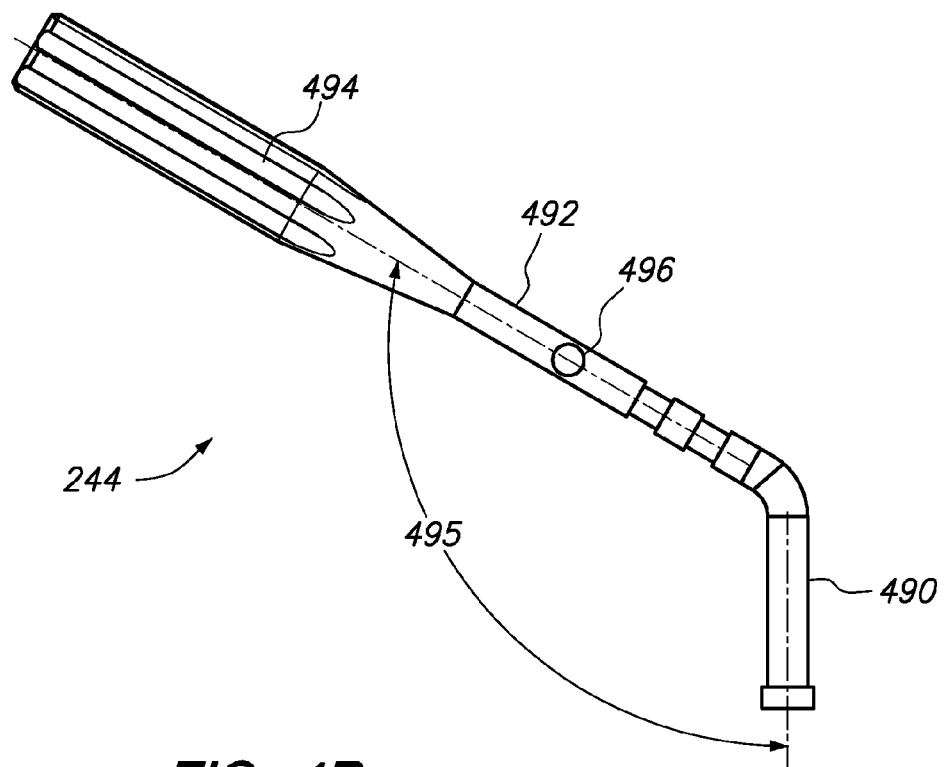
FIG. 4A is a side view of an embodiment of a handle usable as part of the present invention.

FIG. 4A is a side view of an embodiment of a handle 244 usable as part of the present invention. The design of the handle 244 can be varied depending on the specific requirements of the cutting guide 12 (illustrated in FIG. 1A) and the size of the foot 10 (illustrated in FIG. 1A). In this embodiment, the handle 244 is coupled to the housing 242 (as illustrated, for example, in FIG. 2A), has a substantially circular cross-section, and includes a vertical region 490, an angled region 492, and a grip region 494. Alternatively, the handle 244 can have a different design. For example, the handle 244 can have a cross-section that is square shaped, oval shaped, hexagon shaped, or some other shape. Further, the handle 244 can be deigned without the grip region 494. In certain embodiments, the vertical region 490, the angled region 492 and the grip region 494 are formed from a unitary structure. Alternatively, the handle 244 can be made up of individual parts that are joined together.

The vertical region 490 is coupled to the housing top 246 (illustrated in FIG. 2A) of the housing 242 (illustrated in FIG. 2A) and extends in a generally upward direction, perpendicularly away from the housing top 246. In certain embodiments, the vertical region 490 can be approximately 0.56 inches in length. Additionally, the vertical region 490 can have a diameter of approximately 0.125 inches. Alternatively, the vertical region 490 can be greater than or less than 0.56 inches in length, and/or can have a diameter of greater than or less than 0.125 inches.

The angled region 492 extends at a handle angle 495 away from the vertical region 490. In certain embodiments, the angled region 492 can be positioned at a handle angle 495 of approximately 120 degrees relative to the vertical region 490. Stated another way, the angled region 492 can be positioned at an angle of approximately 30 degrees relative to the housing top 246. Alternatively, the angled region 492 can be positioned at a handle angle 495 of greater than or less than 120 degrees relative to the vertical region 490.

Additionally, the angled region 492 can include an aligner aperture 496 that is adapted to receive the aligner 38 (illustrated in FIG. 1A) and assists in coupling the aligner 38 to the handle 244. As illustrated, the aligner aperture 496 can be positioned along the angled region 492 of the handle 244 transversely to the length of the handle 244. For example, in certain embodiments, the aligner aperture 496 can be positioned along the angled region 492 approximately 0.48 inches from the vertical region 490 of the handle 244. Alternatively, the aligner aperture 496 can be positioned along the angled region 492 greater than or less than 0.48 inches from the vertical region 490 of the handle 244.

The grip region 494 extends away from the angled region 492 and generally maintains the same angle relative to the vertical region 490 as the angled region 492. The grip region 494 is designed to be easily gripped, retained and moved by the user of the cutting guide 12. For example, the grip region 494 can include a plurality of grooves along the outer surface of the handle 244.

Figure 4B:
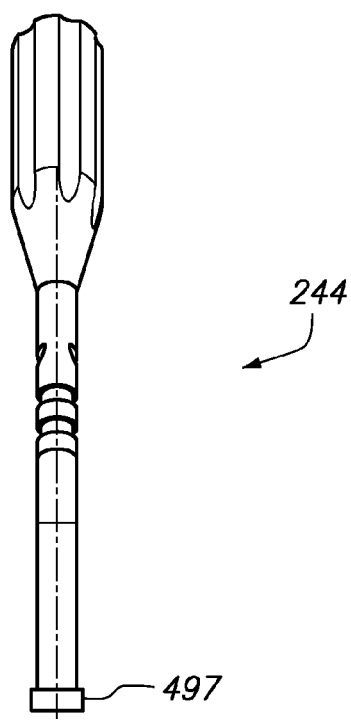
FIG. 4B is a front view of the handle illustrated in FIG. 4A.

FIG. 4B is a front view of the handle 244 illustrated in FIG. 4A. As illustrated, the handle 244 can further include a connector region 497 that is adapted to be connected to the housing top 246 (illustrated in FIG. 2A) of the housing 242 (illustrated in FIG. 2A). The connector region 497 is included in certain embodiments for ease of manufacture. Alternatively, in some embodiments, the handle can be designed without a specific connector region and the vertical region 490 can be directly connected and/or integrally formed with the housing top 246.

In certain embodiments, the connector region 497 can have a diameter of approximately 0.154 inches and have a thickness of approximately 0.06 inches. Alternatively, the connector region 497 can have a diameter of greater than or less than 0.154 inches, and/or can have a thickness of greater than or less than 0.06 inches.

Figure 4C:
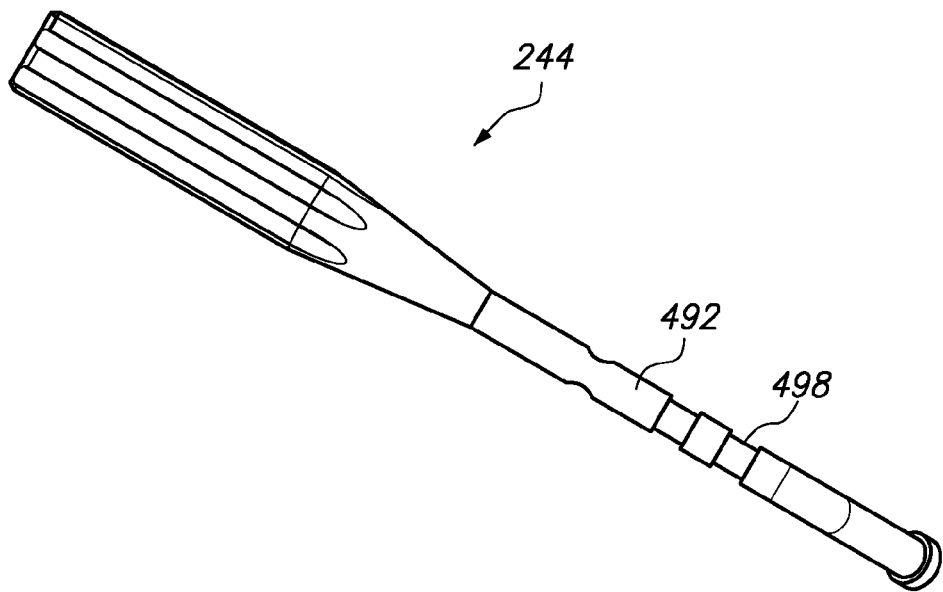
FIG. 4C is a top view of the handle illustrated in FIG. 4A.

FIG. 4C is a top view of the handle 244 illustrated in FIG. 4A. As illustrated, the angled region 492 of the handle 244 can include one or more recessed areas 498. In the embodiment illustrated in FIG. 4C, the handle 244 includes two recessed areas 498 that are each approximately 0.10 inches in length and are recessed approximately 0.01 inches from the majority of the angled region 492 of the handle 244. Alternatively, the recessed areas 498 can each have a length that is greater than or less than 0.10 inches, and/or can be recessed by more than or less than 0.01 inches relative to the majority of the angled region 492 of the handle 244. The recessed areas 498 are included in certain embodiments for purposes of color coding different variations of the cutting guide 12 (illustrated in FIG. 1A). In particular, the recessed areas 498 are adapted to receive paint such that different variations of the cutting guide 12 have recessed areas 498 that are painted different colors. Alternatively, the handle 244 and/or the angled region 492 can be designed without any recessed areas.

FIG. 5 is a side view of a portion of a foot 10 after a metatarsal bone implant 20 has been implanted into a metatarsal 14 that was prepared in part using a cutting guide 12 (illustrated in FIG. 1A) having features of the present invention. In particular, the cutting guide 12 was utilized to guide a saw blade 22 (illustrated in FIG. 1A) to cut away a portion of the metatarsal 14 during preparation of the metatarsal 14 to receive the metatarsal bone implant 20. Subsequently, a hole is drilled into the metatarsal 14 and the metatarsal bone implant 20 is implanted into the hole. As illustrated in FIG. 5, the metatarsal bone implant 20 is implanted within the hole that has been drilled within the distal end 14A of the metatarsal 14, adjacent to the proximal end 16A of the proximal phalanx 16. Positioned in this manner, the metatarsal bone implant 20 effectively forms a part of a metatarsal phalangeal joint 18. In one embodiment, the metatarsal bone implant 20 is sized and shaped to be implanted into the metatarsal of the big toe or great toe, i.e., the first metatarsal 141 (illustrated in FIG. 1B), of the foot 10.

Additionally, with the proper cutting of the metatarsal 14 with use of the cutting guide 12 of the present invention, the metatarsal bone implant 20 can be implanted so as to enable the decompressing of the metatarsal phalangeal joint 18, and to minimize the excessive compression of the metatarsal phalangeal joint 18. The combination of the bone cut and the shape of the metatarsal bone implant 20 creates additional space within the metatarsal phalangeal joint 18 to lessen compressive forces during dorsiflexion of the metatarsal phalangeal joint 18. The decompression is variable or dynamic in that the greater the dorsiflexion, the greater the decompression. Stated in another fashion, there is additional space within the metatarsal phalangeal joint 18 that lessens compressive forces during dorsiflexion of the metatarsal phalangeal joint 18.

Further, with the proper cut in the metatarsal 14, the metatarsal bone implant 20 can be shaped and positioned within the metatarsal 14 to minimize, and properly direct, the weight bearing forces that are transmitted through the metatarsal phalangeal joint 18 and onto the metatarsal bone implant 20.

While a number of exemplary aspects and embodiments of a cutting guide 12 have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A method for guiding a saw blade during preparation of a metatarsal of a foot for a procedure, the foot including one or more additional metatarsals, the method comprising the steps of:
 positioning a housing substantially adjacent to the metatarsal, the housing including a saw guide for receiving and guiding the saw blade;
 coupling an aligner to the housing; and
 aligning the saw guide relative to the metatarsal by aligning the aligner to be substantially parallel to and positioned over a longitudinal axis of one of the one or more additional metatarsals, wherein the step of aligning occurs prior to the act of cutting the metatarsal with the saw blade.

2. The method of claim 1 further comprising the steps of securing a handle to the housing and coupling the aligner to the handle so that the aligner extends substantially perpendicular to the handle.

3. The method of claim 1 wherein the step of positioning includes the step of positioning the housing substantially adjacent to a first metatarsal, and wherein the step of aligning includes the step of aligning the aligner to be substantially parallel to a longitudinal axis of a second metatarsal.

4. The method of claim 1 wherein the step of positioning includes the housing further including a housing top and a housing side, and wherein the saw guide extends through both the housing top and the housing side.

5. The method of claim 4 wherein the step of positioning includes the housing further including a housing axis, and wherein the saw guide extends through the housing side at a guide angle of between approximately 12 degrees and 25 degrees relative to the housing axis.

6. The method of claim 1 wherein the step of coupling includes the aligner extending substantially perpendicular to the saw guide.

7. The method of claim 1 further comprising the step of securing one or more alignment tabs to the housing, the alignment tabs cantilevering in a generally downward direction away from the housing.

8. The method of claim 7 further comprising the step of positioning the alignment tabs within a joint gap between the metatarsal and a proximal phalanx of the foot.

9. The method of claim 1 further comprising the steps of securing one or more retraction tabs to the housing, the retraction tabs extending in a generally upward direction away from the housing, and retracting tendons and skin of the foot with the one or more retraction tabs.

10. The method of claim 1 further comprising the step of securing the housing to the metatarsal with a stabilizer so as to inhibit movement of the housing relative to the metatarsal.

11. A method for guiding a saw blade during preparation of a first metatarsal of a foot for a procedure, the foot including a second metatarsal that is positioned substantially adjacent to the first metatarsal, the method comprising the steps of:
 positioning a housing substantially adjacent to the first metatarsal, the housing including a saw guide for receiving and guiding the saw blade;
 coupling an aligner to the housing; and
 aligning the saw guide relative to the first metatarsal by aligning the aligner to be substantially parallel to and positioned over a longitudinal axis of the second metatarsal, wherein the step of aligning occurs prior to the act of cutting the first metatarsal with the saw blade.

12. The method of claim 11 further comprising the steps of securing a handle to the housing and coupling the aligner to the handle so that the aligner extends substantially perpendicular to the handle.

13. The method of claim 11 wherein the step of positioning includes the housing further including a housing top and a housing side, and wherein the saw guide extends through both the housing top and the housing side.

14. The method of claim 13 wherein the step of positioning includes the housing further including a housing axis, and wherein the saw guide extends through the housing side at a guide angle of between approximately 12 degrees and 25 degrees relative to the housing axis.

15. The method of claim 11 wherein the step of coupling includes the aligner extending substantially perpendicular to the saw guide.

16. The method of claim 11 further comprising the steps of securing one or more alignment tabs to the housing, the alignment tabs cantilevering in a generally downward direction away from the housing, and positioning the alignment tabs within a joint gap between the first metatarsal and a first proximal phalanx of the foot.

17. The method of claim 16 further comprising the steps of securing the housing to the first metatarsal with a first stabilizer so as to inhibit movement of the housing relative to the first metatarsal, and securing the housing to the first proximal phalanx with a second stabilizer so as to inhibit movement of the housing relative to the first proximal phalanx.

18. The method of claim 11 further comprising the steps of securing one or more retraction tabs to the housing, the retraction tabs extending in a generally upward direction away from the housing, and retracting tendons and skin of the foot with the one or more retraction tabs.

* * * * *